United States Patent
Manceau et al.

(10) Patent No.: US 10,271,555 B2
(45) Date of Patent: Apr. 30, 2019

(54) METHOD AND COMPOSITION FOR IMPROVING THE PRODUCTIVITY OF NON-LEGUMINOUS PLANTS

(71) Applicant: LESAFFRE ET COMPAGNIE, Paris (FR)

(72) Inventors: Florian Manceau, Angers (FR); Antoine Martin, Beaucouze (FR); Emmanuel Pajot, Champtocé-sur-Loire (FR); Philippe Pujos, Gradignan (FR); Maud-Cécile Reveillaud, Arvilleé (FR)

(73) Assignee: LESAFFRE ET COMPAGNIE, Paris (FR)

( * ) Notice: Subject to any disclaimer, the term of this patent is extended or adjusted under 35 U.S.C. 154(b) by 114 days.

(21) Appl. No.: 15/316,349

(22) PCT Filed: Jun. 5, 2015

(86) PCT No.: PCT/EP2015/062554
§ 371 (c)(1),
(2) Date: Dec. 5, 2016

(87) PCT Pub. No.: WO2015/185717
PCT Pub. Date: Dec. 10, 2015

(65) Prior Publication Data
US 2018/0177194 A1   Jun. 28, 2018

(30) Foreign Application Priority Data
Jun. 6, 2014 (FR) ...................... 14 55181

(51) Int. Cl.
*A01N 63/04* (2006.01)
*A01G 17/00* (2006.01)
*C12N 1/16* (2006.01)

(52) U.S. Cl.
CPC ........... *A01N 63/04* (2013.01); *A01G 17/005* (2013.01); *C12N 1/16* (2013.01)

(58) Field of Classification Search
None
See application file for complete search history.

(56) References Cited

FOREIGN PATENT DOCUMENTS

| CN | 102108299 | * | 6/2011 |
| CN | 103518779 | * | 1/2014 |
| CN | 103964951 | * | 8/2014 |
| CN | 104230421 | * | 12/2014 |
| FR | 2 873 688 A1 | | 2/2006 |
| FR | 2 901 271 A1 | | 11/2007 |
| ID | 2013001686 | * | 5/2013 |

OTHER PUBLICATIONS

Hafez et al.(Response of some seedlings olive cultivars to foliar spray of yeast and garlic abstracts with or without vascular Arbuscular Mycorrhizal fungi, World Applied Sciences Journal, 2013, 24(9), 1119-1129). (Year: 2013).*
Kobayashi Michiharu et al: "Effect of yeast extracts on higher plants", Plant and Soil, Kluwer Academic Publishers, NL, vol. 57, No. 1, Jan. 1, 1980 (Jan. 1, 1980), pp. 41-47, XP009182370.
M S Hanafy et al: "Effect of Some Natural Extracts on Growth and Chemical Constituents of *Schefflera arboricola* Plants", Journal of Horticultural Science & Ornamental Plants, vol. 4, Jan. 1, 2012 (Jan. 1, 2012), pp. 26-33, XP055167223.
I. Sampedro et al: "Improvement by soil yeasts of arbuscular mycorrhizal symbiosis of soybean (Glycine max) colonized by Glomus mosseae", Mycorrhiza, vol. 14, No. 4, Dec. 18, 2003 (Dec. 18, 2003), pp. 229-234, XP055168237.
Erik Verbruggen et al: "Mycorrhizal fungal establishment in agricultural soils: factors determining inoculation success", New Phytologist, vol. 197, No. 4, Sep. 26, 2012 (Sep. 26, 2012), pp. 1104-1109, XP055167280.
International Search Report and Written Opinion, PCT/EP2015/062554.

* cited by examiner

*Primary Examiner* — Alton N Pryor
(74) *Attorney, Agent, or Firm* — Polsinelli PC

(57) ABSTRACT

The present invention relates to a method for improving the growth, development and productivity of non-leguminous plants using a composition comprising at least one mycorriza and at least one yeast extract, and optionally a substrate; the present invention also relates to such a composition and, when it comprises a substrate, to the process for the production thereof.

17 Claims, No Drawings

METHOD AND COMPOSITION FOR IMPROVING THE PRODUCTIVITY OF NON-LEGUMINOUS PLANTS

RELATED APPLICATIONS

This application is a national stage application (under 35 U.S.C. § 371) of PCT/EP2015/062554, filed Jun. 5, 2015, which claims benefit of French application FR 1455181, filed Jun. 6, 2014.

FIELD OF THE INVENTION

The present invention relates to the field of the cultivation of plants, in particular that of the cultivation of non-leguminous plants. More particularly, the present invention relates to a method for improving the productivity of non-leguminous plants using at least one mycorriza and at least one yeast extract, and also to a composition comprising a combination of mycorriza(e) and yeast extract(s), and optionally a substrate.

PRIOR ART

Agriculture is constantly seeking to improve crop productivity, in order to improve the competitiveness of the economical actors and to meet the increasing market needs. This improvement involves, on the one hand, increasing yields and improving qualitative characteristics, and on the other hand, reducing the volumes and costs of the inputs used to produce a production unit. Furthermore, with the aim of protecting the environment, and of introducing sustainable agricultural practices, many research studies are aimed at increasing productivity without increasing provision of chemical inputs, or even by reducing them. One way of achieving these objectives is to use symbiotic microorganisms which help the roots of the plant to use the available resources most effectively. The most common method for doing this is to increase the population of these microorganisms by providing selected strains or strains collected locally and multiplied industrially. These provisions of inoculum are carried out in proximity to the roots, for example by addition to the soil or by incorporation into a substrate, or by treating seeds. Use is thus made of *Rhizobium* sp bacteria, which make it possible to transfer atmospheric nitrogen to the plants, or mycorrizal fungi, which attach to the roots of the plants and provide them with minerals and water.

In particular, E Verbruggen et al. (New Phytologist Volume 197, Issue 4, pages 1104-1109, March 2013) indicates that the use of mycorrizae improves plant productivity. Furthermore, Sampedro et al. (Mycorriza. 2004 August; 14(4):229-34) describes a favourable effect of living yeasts on mycorrizal spore lengths.

Inoculation of the roots with mycorrizal fungi makes it possible to increase the productivity of the plant. However, the effects obtained are sometimes insufficient, which curbs the development of this technique, and it is necessary to improve the method so that it more successfully meets the requirements of its users.

For this purpose, a process has been developed which is aimed at improving the biomass production of non-leguminous plants by applying to the soil innocula of mycorrizae and of inactive yeasts (FR 2 901 271).

FR 2 901 271 shows that the inactive yeasts exert a beneficial action on the non-leguminous plant crops by application to the soil with mycorrizae. This result proves to be surprising, according to the proprietor of this patent application, since, according to said proprietor, it was known that the use of dead yeasts (inactive yeasts are dead yeasts) or of yeast fractions had no effect on the mycorrization of non-leguminous plants.

Thus, for those skilled in the art, according to this teaching, yeast fractions (for example yeast walls or yeast extracts) have no effect on the mycorrization of non-leguminous plants. *A fortiori*, yeast extracts (which are yeast fractions) have no effect on the mycorrization of non-leguminous plants.

Moreover, Kobayashi et al. (Plant and Soil 1980, Volume 57, Issue 1, pp. 41-47) describes a composition comprising a *Saccharomyces cerevisiae* yeast extract extracted by autolysis for improving the growth of a plant ("vineless pea"), it being understood that peas are generally leguminous plants.

Hanafy et al. (Plants Journal of Horticultural Science & Ornamental Plants 4 (1): 26-33, 2012) describes the effect of a *Saccharomyces cerevisiae* yeast extract on the growth of a tropical tree *Schefflera*. FR 2 873 688 describes the use of active or inactive yeasts for improving the nutrition of tomatoes or of grass.

However, none of these documents either mentions or suggests that the yeast extracts might have effects on mycorrization when they are applied with mycorrizae.

Moreover, these documents do not suggest that the combined use of yeast extracts or of mycorriza can make it possible to observe a synergistic effect, as shown in an example of the present application.

Going against the prejudice of those skilled in the art, the applicant has tested combinations of yeast extract and of mycorriza and has noted, surprisingly since it is completely contrary to the prior teaching, that they have a beneficial effect, both as such and mixed with a substrate, and that the use of such a substrate enriched with yeast extract and mycorrizae makes it possible to obtain at least one of the following surprising results:

- an improvement in the mycorrization of non-leguminous plant crops, which is a means for improving the other parameters,
- an improvement in the rooting of non-leguminous plant crops,
- an improvement in the growth of non-leguminous plant crops,
- an improvement in the flowering (amount and earliness) of non-leguminous plant crops,
- an improvement in the fresh biomass of non-leguminous plant crops,
- an improvement in the dry biomass of non-leguminous plant crops,
- an improvement in the yields of non-leguminous plant crops,
- an improvement in the mineral nutrition of non-leguminous plants,
- an improvement in the hydric nutrition and in the resistance to hydric stress.

Founded on the incredible effectiveness of these results, a subject of the present invention is a method for improving at least one of the parameters above using a composition comprising at least one mycorriza and at least one yeast extract.

Definitions

In the present invention, the terms below are defined in the following way:

The term "yeast extract" refers to the content of the yeast cells, said content being obtained by any suitable extraction process known to those skilled in the art. According to one embodiment, the yeast extract according to the invention is obtained by a process selected from the group comprising plasmolysis, autolysis, and the combination of plasmolysis and autolysis, preferably autolysis. Advantageously, a proteolytic enzyme may be added during the extraction process in order to increase the efficiency of said process.

The term "yeast fraction" covers substances obtained by separation of the shell and of the rest of the yeast cell; for example, the "yeast cell wall" fraction corresponds to the shells of the yeast cells with the exclusion of the content of the cells; the "yeast extract" fraction corresponds to the content of the yeast cells with the exclusion of the shells.

The term "inactive yeasts" refers to yeasts that have been killed, by any physical, chemical or physicochemical process. Most commonly, the yeasts are killed by heat shock at the end of the production process, then dried.

The term "yeast derivatives" covers all of the yeast-based products: fractions, inactive yeasts, and other compositions.

The term "mycorriza" refers to a symbiotic association between mycelial filaments of fungi and roots of plants. The external filaments of the mycelium combine with the roots of the plants and thus constitute an actual elongation of the root system that will explore the soil in the periphery of the root. The mycelial network in the soil can thus reach several million km/hectare, multiplying the area explored by the roots by 20 to 25 times. The mycelium is not partitioned, thus fluidizing the transfers. By extension, the term "mycorriza" covers herein the term "mycorrizal fungus".

The term "propagule" is used to denote simultaneously the spores, the vesicles and the fragments of roots containing vesicles, since all these structures serve to propagate the species. Indeed, the mycorrizal fungus forms spores (isolated or grouped together in sporocarps) intended to propagate and disseminate the species. In certain species, reproductive structures, called intra-root vesicles, differentiate in the root cortex and have properties similar to those of spores (Les mycorhizes, La nouvelle revolution verte [Mycorrizae, The new green revolution] J. Fortin, C. Plenchette, Y. Piché 2008).

The term "substrate" refers to a culture support, namely a set of products intended to serve as a culture medium for certain plants. Their use results in the formation of media having a porosity in air and in water such that they are capable of both anchoring the absorbent organs of plants and enabling them to be in contact with the solutions required for their growth. They are generally composed of organic matter and of inorganic matter. They are generally composed of peat (organic matter often predominant), of other organic materials (in particular coconut fibres, barks, wood fibres, green waste composts), and of inorganic materials (sands, pozzolans, clays, mineral wools, perlite, vermiculite). In the present description, the term "substrate" not preceded by an adjective relates to a product which contains neither mycorriza nor yeast extract; the term "inoculated substrate" relates to a substrate to which at least one mycorriza has been added; the term "enriched substrate" relates to a system comprising a substrate, at least one mycorriza and at least one yeast extract.

The term "degree of mycorrization" represents the level of mycorrizal infection of the roots of the plant observed. There are two different methods for evaluating mycorrizal infection: the method of Giovannetti and Mosse (1980) and that of Trouvelot et al. (1986). The method of Giovannetti and Mosse is particularly suitable for the rapid evaluation of the mycorrizal infection of the roots and provides a degree of mycorrization. The second method, Trouvelot et al., which is more complete but longer, makes it possible to calculate the degree of mycorrization, the degree of mycorrization and the arbuscule- and vesicle-richness of a sample. It is this method that was used for the tests described by the applicant.

The term "non-leguminous plants" means a plant of which the fruit is not a pod and which does not belong to the family Fabaceae.

The term "biomass" means all of the matter, organic and mineral, constituting a plant.

The term "approximately" placed before a numerical value means plus or minus 10% of this numerical value.

DESCRIPTION

Thus, the present invention relates to a method for improving the growth and/or development and the productivity of non-leguminous plants, comprising the administration or the provision of a composition comprising at least one mycorriza and at least one yeast extract.

According to the invention, the improving of the growth and/or development and of the productivity of non-leguminous plant crops includes improving at least one of the following parameters: the degree of mycorrization, the rooting, the growth of the plants, the height of the plants, the flowering, in particular in terms of amount or in terms of earliness, the fresh biomass, the dry biomass, the yield, the mineral nutrition, the hydric nutrition or the resistance to abiotic stresses, in particular to hydric stress.

According to one embodiment of the present invention, the method does not comprise the addition of compost or of compost extract.

The invention is applicable to non-leguminous plants of any type, and in particular to grasses (graminaceous plant) and dicotyledons, to annual, biennial and perennial plants, to vegetables, to cereals, including wheat, barley, rice, maize, spelt, oats, fonio, rye, sorghum (in particular Friggo) and millet, to oil-producing plants, to potatoes, to sugar cane, to bananas, to pineapples, to cocoa, to coffee, to tobacco, to ligneous plants, to fruit or non-fruit trees, to vines, and to ornamental plants (in particular Zellino® Rose Fluo geranium).

According to the invention, the mycorrizae comprise an active strain of endomycorrizal and/or ectomycorrizal fungi. Preferably, the mycorrizae used in the process of the invention comprise one or more active strains of an endomycorrizal fungus, more particularly of the endomycorrizal fungus of the order Glomerales. Among glomerals, mention may be made of the genus *Glomus* sp (newly named *Sclerocystis* sp; Schüßler and Walker, 2010), and more specifically the strain *Glomus* sp coded LPA Val1, which is the active principle of the Solrize® product developed and sold by the company Agrauxine. The Solrize® product is in granule form and contains the endomychorrizal fungus *Sclerocystis* sp (formerly *Glomus* sp) at a minimum concentration of 10 propagules per gram.

The yeast extract used in the present invention is obtained by plasmolysis or autolysis, or a combination of plasmolysis and autolysis of yeasts, in particular of the genus *Saccharomyces, Kluyveromyces, Candida* or *Torula*, preferentially *S. cerevisiae*.

According to another embodiment, the methods for extracting yeasts can be reinforced by the addition of additives such as enzymes, in particular proteolytic enzymes, or chemical compounds, in particular sulphites.

The yeast extracts used in the invention may come from all species of yeasts, in particular the yeasts of the genus *Saccharomyces*, in particular *S. cerevisiae*. More particularly, the yeast extracts are of the type of those sold by the company Agro-Levures et Dérivés.

The invention also comprises a composition comprising at least one mycorriza and at least one yeast extract.

It is thus possible to envisage a composition consisting of a substrate supplemented with at least one mycorriza and at least one yeast extract, in which the non-leguminous plants can be directly planted.

According to one embodiment of the invention, the mycorriza/yeast extract weight ratio is between 0.01 and 100, preferentially between 0.05 and 20, more preferentially between 0.1 and 10. In another embodiment, the mycorriza/yeast extract weight ratio is equal to approximately 16, approximately 8, approximately 4 or approximately 2.

The amount of mycorrizae in the composition of the invention is between 0.1 and 15 $kg/m^3$, preferentially between 0.5 and 8 $kg/m^3$, more preferentially between 1 and 4 $kg/m^3$ of the composition.

In another embodiment, the amount of mycorrizae in the composition is equal to approximately 2 $kg/m^3$, approximately 4 $kg/m^3$ or approximately 8 $kg/m^3$.

The amount of yeast extract in the composition of the invention is between 0.1 and 10 $kg/m^3$, preferentially between 0.2 and 5 $kg/m^3$, more preferentially between 0.4 and 2 kg of dry matter per $m^3$ of substrate. According to another embodiment, the amount of yeast extract is approximately 0.5 $kg/m^3$ or approximately 1 $kg/m^3$ of enriched substrate.

According to one particular embodiment, the composition of the present invention does not comprise compost or compost extract. According to one embodiment, the composition of the invention does not comprise a bacterium.

According to one embodiment, the composition according to the invention may be in wettable powder (WP), granule (WG) or liquid form.

According to another embodiment, the yeast extract and the mycorriza are administered simultaneously or successively, by application to the soil (spraying, spreading, sprinkling, fertigation, dropwise, in the seed drill or in the open field), by root dipping, by seed treatment or by incorporation into a cultivation support or by any means which makes it possible to bring the composition into contact, immediately or in the future, with the roots to be inoculated.

According to one embodiment, the mycorriza and the yeast extract used in the present invention are mixed in the same container or placed in two separate containers.

According to one embodiment of the invention, the amount of mycorrizae provided per hectare is between 0.1 and 100 kg/ha, preferentially between 0.3 and 50 kg/ha, more preferentially between 0.5 and 20 kg/ha.

In another embodiment, the amount of yeast extract provided per hectare according to the invention is between 0.1 and 50 kg/ha, preferentially between 0.5 and 20 kg/ha, more preferentially between 1 and 10 kg of dry matter per hectare.

According to one embodiment, the composition according to the invention comprises at least one mycorriza and at least one yeast extract and a substrate.

In this embodiment, the composition is preferentially in solid form, in particular in particulate solid form, and, in certain embodiments, in powder form.

Advantageously, said substrate comprises, in a non-limiting manner, pure clay and/or peat, sand, pozzolan, perlite, wood fibre, coconut fibre, blonde peat, black peat, heath earth, barks, vermiculite, magnesia, lime, wool. Said substrate may be an organic amendment, a planting substrate, a flowering substrate, or any other agricultural substrate. According to one embodiment, the substrate is a culture support of the type of those sold by specialists for professional horticulturists.

A subject of the invention is thus a medium for planting or cultivating a non-leguminous plant, comprising at least one mycorriza and at least one yeast extract and, optionally, substrate.

The invention also relates to a process for producing a composition comprising at least one mycorriza and at least one yeast extract, in which said mycorriza and said yeast extract are mixed. The invention also relates to a process for producing an enriched substrate according to the invention, which comprises simultaneously or successively incorporating mycorrizae and yeast extracts into the substrate.

The invention also relates to a process for producing an enriched substrate according to the invention, comprising, in a first step, mixing mycorrizae with a substrate, and then adding at least one yeast extract.

According to one embodiment of the present invention, the improvement in the degree of mycorrization of the plants placed in the enriched substrate means that the mycorrization is increased by 10% to 150%, preferably by 12% to 90%, more preferentially by 15% to 70% relative to the mycorrization obtained if the plant is placed in a non-enriched substrate.

According to another embodiment, the improvement in the height of the plants placed in the enriched substrate means that the height of the plants is increased by 10% to 150%, preferably by 12% to 110%, more preferentially by 15% to 80% relative to the height of the plant observed if said plant is placed in a non-enriched substrate.

According to another embodiment, the improvement in the fresh and dry biomass of the plants placed in the enriched substrate means that the fresh or dry biomass is increased by 5% to 250%, preferably by 20% to 200%, more preferentially by 30% to 160% relative to the fresh or dry biomass obtained if the plant is placed in a non-enriched substrate.

According to another embodiment, the improvement in the floriferous quality of the plants placed in the enriched substrate means that the number of flower buds is increased by 10% to 150%, preferably by 15% to 100%, more preferentially by 20% to 80% relative to the number of flower buds observed if the plant is placed in a non-enriched substrate.

EXAMPLES

The present invention will be understood more clearly on reading the following examples which illustrate the invention in a non-limiting manner.

1. Materials and Methods

The materials and methods are common to the four examples presented.

Number of Trials:

Four trials were carried out, one on geranium (example 1), two on sorghum (examples 2 and 3) and one on *chrysanthemum* (example 4).

Site:

The trials were carried out in a greenhouse, in Angers, France.

Plant Material:

The tests were carried out on three types of plants: Friggo sorghum, Zellino® Rose Fluo geranium and *chrysanthemum*.

Yeast Products:

Yeast extracts: Lev1 extract and Lev2 extract

Inactive yeasts: INACT1

Mycorriza:

The mycorrizae used correspond to the Solrize® Pro product sold by the company Agrauxine. They contain an active strain of the endomycorrizal fungus *Glomus* sp.

Substrate:

The substrate used has the following composition: pure clay, sand, pozzolan, perlite, peat.

Trial Device and Modes:

four repeats per mode with one plant per pot/repetition, i.e. four plants per mode.

The mycorrizae used (Solrize® Pro) were tested at 1, 2 or 3 doses: DN (8 kg/m$^3$), DN/2 (4 kg/m$^3$, DN/3 (2.7 kg/m$^3$).

The yeast extracts (Lev1 extract and Lev2 extract) were tested at 1 kg/m$^3$.

The inactive yeast (INACT1) was tested at 1 kg/m$^3$.

Evaluation of the Trials:

The trials will be evaluated by measuring the following quantitative parameters:

Degree of mycorrization of the root system;

Measurement of the height of the plants (except example 1);

Weight of the total biomass, fresh and dry (except example 1);

Number of flower buds (only example 4).

2. Results

The mycorrizae are mixed manually with the substrate at concentrations of 8, 4 or 2.7 kg/m$^3$ of substrate. The yeast extracts (Lev1 extract and Lev2 extract) or the inactive yeasts (INACT1) are then added to the substrate inoculated.

Example 1 (Geranium): Yeast Extract Vs Inactive Yeasts Comparison

Effect on the Degree of Mycorrization (DM) as %

TABLE 1A

| Evaluation of the degree of mycorrization of geranium | | |
|---|---|---|
| Solrize dose: | DN | DN/2 |
| Solrize ® Pro alone | 26.9 | 21.0 |
| Solrize ® Pro + Lev1 extract (1 kg/m$^3$) | 37.0 | 27.6 |
| Solrize ® Pro + INACT1 (1 kg/m$^3$) | 18.5 | 12.8 |
| Lev1 extract 1 kg: Increase DM/Solrize | 37% | 31% |
| INACT1 1 kg: Increase DM/Solrize | −31% | −39% |

Table 1A shows that the combination of yeast extracts (Lev1 extract) and mycorrizae significantly increases the degree of mycorrization of geranium (+31-37%). Conversely, the inactive yeasts show a negative effect on the degree of mycorrization of geranium. No mycorrization is observed when a yeast extract alone is used.

Example 2 (Sorghum): Comparison Between Yeast Extract and Inactive Yeasts

Effect on the Degree of Mycorrization (DM) as %

TABLE 2A

| Evaluation of the degree of mycorrization of sorghum | | |
|---|---|---|
| Solrize dose: | DN | DN/2 |
| Solrize ® Pro alone | 28.8 | 21.2 |
| Lev1 extract alone (1 kg/m$^3$)* | 0 | 0 |
| Solrize ® Pro + Lev1 extract (1 kg/m$^3$) | 48.4 | 34.4 |
| Solrize ® Pro + Lev1 extract (0.5 kg/m$^3$) | 38.5 | 29.8 |
| Solrize ® Pro + INACT1 (1 kg/m$^3$) | 10.6 | 14.2 |
| Lev1 extract 1 kg: Increase DM/Control | 68% | 62% |
| INACT1 1 kg: Increase DM/Control | −63% | −33% |

*this line corresponds to the results observed for the yeast extract alone without Solrize ® Pro.

Table 2A confirms the results observed on geranium: the combination of yeast extracts (Lev1 extract) and mycorrizae significantly increases the degree of mycorrization of sorghum (+62-68%). Conversely, the inactive yeasts show a negative effect on the degree of mycorrization of sorghum.

The yeast extract alone (or the absence of product, negative control) does not enable any mycorrization to be observed. An increase in mycorrization is also observed when lower doses of yeast extract are used.

Effect on the Height of the Plants (HP) in Cm, at 6 Weeks and at 10 Weeks

TABLE 2B

| Evaluation of the height of the sorghum plants, 6 weeks and 10 weeks after sowing | | | | |
|---|---|---|---|---|
| | 6 weeks after sowing | | 10 weeks after sowing | |
| Solrize dose | DN | DN/2 | DN | DN/2 |
| Solrize ® Pro | 29.8 | 33.2 | 48.9 | 46.8 |
| Lev1 extract alone (1 kg/m$^3$)* | | | 53.5 | 53.5 |
| Solrize ® Pro + Lev1 extract (1 kg/m$^3$) | 41.3 | 41.0 | 64.8 | 58.2 |
| Soirize ® Pro + INACT1 (1 kg/m$^3$) | 36.0 | 38.7 | 50.9 | 49.9 |
| Lev1 extract 1 kg: Increase DM/Solrize | 38% | 24% | 33% | 24% |
| INACT1 1 kg: Increase DM/Solrize | 21% | 17% | 4% | 7% |

*this line corresponds to the results observed for the yeast extract alone without Solrize ® Pro.

Table 2B shows that the combination of yeast extracts (Lev1 extract) and mycorrizae significantly increases the growth (height) of sorghum (+24-38%). This surprising effect observed is much greater than that observed with the combination of inactive yeasts and mychorrhizae.

Moreover, a synergistic effect is observed when the yeast extract is used in combination with the mycorriza.

Effect on the Height of the Plants (HP) in Cm, at 10 Weeks

|  | 10 weeks after sowing | |
| --- | --- | --- |
| Solrize dose: | DN | DN/2 |
| Negative control | 49.3 | 49.3 |
| Solrize ® Pro | 48.9 | 46.8 |
| Lev1 extract alone (0.5 kg/m$^3$)* | 48.0 | 48.0 |
| Solrize ® Pro + Lev1 extract (0.5 kg/m$^3$) | 55.1 | 46.5 |

A synergistic effect is also observed when the yeast extract is used at a lower dose, in combination with the mycorriza at the usual dose (DN).

Weight of Fresh Biomass (FB) and Dry Biomass (DB), in g

TABLE 2C

Evaluation of fresh and dry sorghum biomass, 10 weeks after sowing

|  | FB | | DB | |
| --- | --- | --- | --- | --- |
| Solrize dose: | DN | DN/2 | DN | DN/2 |
| Solrize ® Pro alone | 3.4 | 3.9 | 0.7 | 0.8 |
| Lev1 extract alone (1 kg/m$^3$)* | 6.0 | 6.0 | 1.1 | 1.1 |
| Solrize ® Pro + Lev1 extract (1 kg/m$^3$)* | 8.0 | 8.4 | 1.6 | 1.8 |
| Solrize ® Pro + INACT1 (1 kg/m$^3$) | 5.7 | 6.5 | 1.2 | 1.2 |
| Lev1 extract 1 kg: Increase DM/Solrize | 139% | 118% | 129% | 124% |
| INACT1 1 kg: Increase DM/Solrize | 62% | 67% | 71% | 50% |

*this line corresponds to the results observed for the yeast extract alone without Solrize ® Pro.

Table 2C shows that the combination of yeast extracts (Lev1 extract) and mycorrizae very significantly increases the fresh and dry sorghum biomass (+118-145%). This surprising effect observed is much greater than that observed with the combination of inactive yeasts and mycorrizae (+59-71%).

Example 3 (Sorghum): Comparison of Two Yeast Extracts

Effect on the Degree of Mycorrization (DM) as %

TABLE 3A

Evaluation of the degree of mycorrizatian of sorghum

| Solrize dose: | DN |
| --- | --- |
| Solrize ® Pro | 27.9 |
| Solrize ® Pro + Lev1 extract (1 kg/m$^3$) | 38.5 |
| Solrize ® Pro + Lev2 extract (1 kg/m$^3$) | 35.6 |
| Lev1 extract 1 kg: Increase DM/Control | 38% |
| Lev2 extract 1 kg: Increase DM/Control | 28% |

Table 3A confirms the results observed in examples 1 and 2: the combination of yeast extracts (Lev1 extract or Lev2 extract) and mycorrizae significantly increases the degree of mycorrization of sorghum (+28-38%).

Effect on the Height of the Plants (HP) in Cm, at 10 Weeks

TABLE 3B

Evaluation of the height of the sorghum plants, 10 weeks after sowing

| Solrize dose: | 6 weeks after sowing DN |
| --- | --- |
| Solrize ® Pro | 54.4 |
| Solrize ® Pro + Lev1 extract (1 kg/m$^3$) | 68.4 |
| Solrize ® Pro + Lev2 extract (1 kg/m$^3$) | 66.1 |
| Lev1 extract 1 kg: Increase HP/Control | 26% |
| Lev2 extract 1 kg: Increase HP/Control | 22% |

Table 3B confirms the results observed in example 2: the combination of the yeast extracts (Lev1 extract or Lev2 extract) and mycorrizae significantly increases the growth (height) of sorghum (+22-26%).

Weight of Fresh Biomass (FB) and Dry Biomass (DB), in g

TABLE 3C

Evaluation of fresh and dry sorghum biomass, 10 weeks after sowing

| Solrize dose: | Fresh biomass (FB) in g DN | Dry biomass (DB) in g DN/2 |
| --- | --- | --- |
| Solrize ® Pro | 7.7 | 1.9 |
| Solrize ® Pro + Lev1 extract (1 kg/m$^3$) | 13.1 | 3.1 |
| Solrize ® Pro + Lev2 extract (1 kg/m$^3$) | 12.4 | 2.9 |
| Lev1 extract 1 kg: Increase FB & DB/Control | 70% | 63% |
| Lev2 extract 1 kg: Increase FB & DB/Control | 61% | 53% |

Table 3C confirms the results observed in example 2: the combination of the yeast extracts (Lev1 extract or Lev2 extract) and mycorrizae significantly increases the fresh and dry sorghum biomass (+53-70%).

In conclusion, the two yeast extracts tested both showed very advantageous effects in combination with mycorrizae.

Example 4 (*Chrysanthemum*)

Effect on the Degree of Mycorrization (DM) as %

TABLE 4A

Evaluation of the degree of mycorrization of chrysanthemum

| Solrize dose: | DN | DN/2 | DN/3 |
| --- | --- | --- | --- |
| Solrize ® Pro+ | 29.0 | 22.1 | 18.8 |
| Solrize ® Pro + Lev1 extract (1 kg/m$^3$) | 39.5 | 31.9 | 28.0 |
| Lev1 extract 1 kg: Increase DM/Control | 36% | 44% | 49% |

Table 4A confirms the results observed on geranium and sorghum: the combination of yeast extracts (Lev1 extract) and mycorrizae significantly increases the degree of mycorrization of *chrysanthemum* after 14 weeks (+36-49%), and makes it possible to reduce the mycorriza dose to DN/3 while at the same time retaining a good degree of mycorrization. The use of the yeast extract alone does not enable any mycorrization to be observed.

Effect on the Height of the Plants (HP) in Cm, at 10 Weeks

TABLE 4B

Evaluation of the height of the chrysanthemum plants, at 10 weeks

| Solrize dose: | DN | DN/2 | DN/3 |
|---|---|---|---|
| Solrize ® Pro | 12.3 | 10.5 | 11.3 |
| Solrize ® Pro + Lev1 extract (1 kg/m³) | 17.5 | 14.8 | 17.3 |
| Lev1 extract 1 kg: Increase DM/Control | 42% | 41% | 53% |

Table 4B confirms the results observed on geranium and sorghum: the combination of yeast extracts (Lev1 extract) and mycorrizae significantly increases the growth (height) of *chrysanthemum* (+41-53%) after 14 weeks.

Weight of Fresh Biomass (FB) and Dry Biomass (DB), in g

TABLE 4C

Evaluation of fresh and dry chrysanthemum biomass, at 10 weeks

| | Fresh biomass (FB) in g | | | Dry biomass (DB) in g | | |
|---|---|---|---|---|---|---|
| Solrize dose: | DN | DN/2 | DN/3 | DN | DN/2 | DN/3 |
| Solrize ® Pro | 29.6 | 29.0 | 26.3 | 5.7 | 5.5 | 4.9 |
| Lev1 extract (1 kg/m³) | 29.6 | 29.6 | 29.6 | 7.1 | 7.1 | 7.1 |
| Solrize ® Pro + Lev1 extract (1 kg/m³) | 31.3 | 31.8 | 30.2 | 7.6 | 7.2 | 6.8 |
| Lev1 extract 1 kg: Increase FB & DB/Control | 6% | 10% | 15% | 33% | 31% | 39% |

Table 4C confirms the results observed on geranium and sorghum: the combination of yeast extracts (Lev1 extract) and of mycorrizae significantly increases the fresh and dry *chrysanthemum* biomass (+6-39%).

Effect on Flowering (Number of Flower Buds)

TABLE 4D

Evaluation of the number of chrysanthemum flower buds

| Solrize dose: | DN | DN/2 | DN/3 |
|---|---|---|---|
| Solrize ® Pro | 2 | 2.5 | 1.5 |
| Solrize ® Pro + Lev1 extract (1 kg/m³) | 3 | 3.8 | 3.5 |
| Lev1 extract 1 kg: Increase DM/Control | 50% | 52% | 133% |

Table 4D shows that the combination of yeast extracts (Lev1 extract) and mycorrizae significantly increases the number of *chrysanthemum* flower buds (more than 50%).

Example 5: *Hibiscus*

Effect on Flowering (Number of Flower Buds)

TABLE 5

Evaluation of the number of hibiscus flower buds

| Solrize dose (in kg/m³) | 1.2 | 1.0 |
|---|---|---|
| Solrize ® Pro | 3.7 | 3.3 |
| Lev1 extract (1 kg/m³) | 5.3 | 5.3 |
| Solrize ® Pro + Lev1 extract (1 kg/m³) | 8 | 6.7 |

Table 5 shows that the combination of yeast extracts (Lev1 extract) and mycorrizae significantly increases the number of *hibiscus* flower buds.

The invention claimed is:

1. A method for improving growth and/or development and productivity of non-leguminous plants, the method comprising applying a composition comprising a synergistically effective amount of at least one mycorriza and at least one yeast extract to the non-leguminous plants, thereby synergistically improving the growth and/or development and the productivity of the non-leguminous plants, wherein the at least one mycorriza comprises an endomycorrizal fungus *Sclerocystis* sp., and the at least one yeast extract is derived from *Saccharomyces, Kluyveromyces, Candida*, or *Torula* and is a content of the yeast cells, obtained by a process selected from plasmolysis, autolysis, and a combination of plasmolysis and autolysis of yeast.

2. The method according to claim 1, in which the improving of the growth and/or development of non-leguminous plants includes improving at least one of the following parameters: the degree of mycorrization, the rooting, the growth of the plants, the height of the plants, the flowering, the fresh biomass, the dry biomass, the yield, the mineral nutrition, and the hydric nutrition or the resistance to abiotic stresses.

3. The method according to claim 1, in which the non-leguminous plants are selected from the group consisting of grasses, dicotyledons, annual, biennial and perennial plants, vegetables, cereals, oil-producing plants, potatoes, sugar canes, bananas, pineapples, cocoa, coffee, tobacco, ligneous plants, fruit or non-fruit trees, vines, and ornamental plants.

4. The method according to claim 1, in which the at least one mycorriza comprises an active strain of the endomycorrizal fungus.

5. The method according to claim 1, wherein the at least one yeast extract is the content of yeast cells, obtained by a process selected from plasmolysis, autolysis, or a combination of plasmolysis and autolysis of yeast in presence of a proteolytic enzyme.

6. The method according to claim 1, in which the at least one yeast extract and the at least one mycorriza are administered simultaneously or successively, by application to the soil, by root dipping, by seed treatment or by incorporation into a cultivation support or by any means which makes it possible to bring the composition into contact, immediately or in the future, with the roots to be inoculated.

7. The method according to claim 1, in which the yeast extract is derived from *S. cerevisiae*.

8. A composition comprising a synergistically effective amount of at least one mycorriza and at least one yeast extract, wherein the at least one mycorriza comprises endomycorrizal fungus *Sclerocystis* sp., and the at least one yeast extract is derived from *Saccharomyces, Kluyveromyces, Candida*, or *Torula*, and the composition synergistically improves growth and/or development and productivity of non-leguminous plants, wherein the extract is a content of yeast cells obtained by a process selected from plasmolysis, autolysis and a combination of plasmolysis and autolysis of yeast.

9. The composition according to claim 8, further comprising a substrate.

10. The composition according to claim 9, in which the amount of the mycorrizae is between 0.1 and 15 kg/m$^3$ of the composition.

11. The composition according to claim 9, in which the amount of yeast extract is between 0.1 and 10 kg/m$^3$ of the composition.

12. The composition according to claim 9, in which the substrate comprises organic matter and inorganic matter.

13. A process for producing a composition according to claim 9 comprising simultaneously or successively incorporating the at least one mycorriza and the at least one yeast extract with a substrate.

14. The composition according to claim 9, in which the amount of the mycorrizae is between 0.5 and 8 kg/m$^3$ of the composition.

15. The composition according to claim 9, in which the amount of the mycorrizae is between 1 and 4 kg/m$^3$ of the composition.

16. The composition according to claim 9, in which the amount of the yeast extract is between 0.2 and 5 kg/m$^3$ of the composition.

17. The composition according to claim 9, in which the amount of the yeast extract is between 0.4 and 2 kg/m$^3$ of the composition.

* * * * *